United States Patent [19]

Chin

[11] Patent Number: 4,630,609

[45] Date of Patent: Dec. 23, 1986

[54] DILATATION CATHETER METHOD AND APPARATUS

[75] Inventor: Albert K. Chin, San Franscisco, Calif.

[73] Assignee: Thomas J. Fogarty, Palo Alto, Calif.

[21] Appl. No.: 263,776

[22] Filed: May 14, 1981

[51] Int. Cl.⁴ .......................................... A61M 29/02
[52] U.S. Cl. ..................................... 128/344; 604/101
[58] Field of Search ............... 128/344, 325, 349 B, 128/349 BV, DIG. 25; 604/101

[56] References Cited

U.S. PATENT DOCUMENTS

| | | | |
|---|---|---|---|
| 805,851 | 11/1905 | Goldfarb . | |
| 2,493,326 | 1/1950 | Trinder | 128/325 |
| 2,912,981 | 11/1959 | Keough | 128/349 B |
| 3,435,826 | 4/1969 | Fogarty | 128/348 |
| 3,467,101 | 9/1969 | Fogarty et al. | 128/348 |
| 3,467,102 | 9/1969 | Fogarty et al. | 128/348 |
| 3,525,329 | 8/1970 | Zeimer | 128/2 |
| 3,766,924 | 10/1973 | Pidgeon | 128/325 |
| 3,896,815 | 7/1975 | Fettel et al. | 128/348 |
| 4,254,774 | 3/1981 | Boretos | 128/344 |

FOREIGN PATENT DOCUMENTS 512456  9/1979  United Kingdom ............... 128/344

Primary Examiner—Michael H. Thaler
Attorney, Agent, or Firm—Limbach, Limbach & Sutton

[57] ABSTRACT

A dilatation catheter is provided at its distal end with an invertable-evertable balloon which expands longitudinally and then radially and is provided at the proximal side of that balloon with a sleeve balloon which expands radially.

5 Claims, 6 Drawing Figures

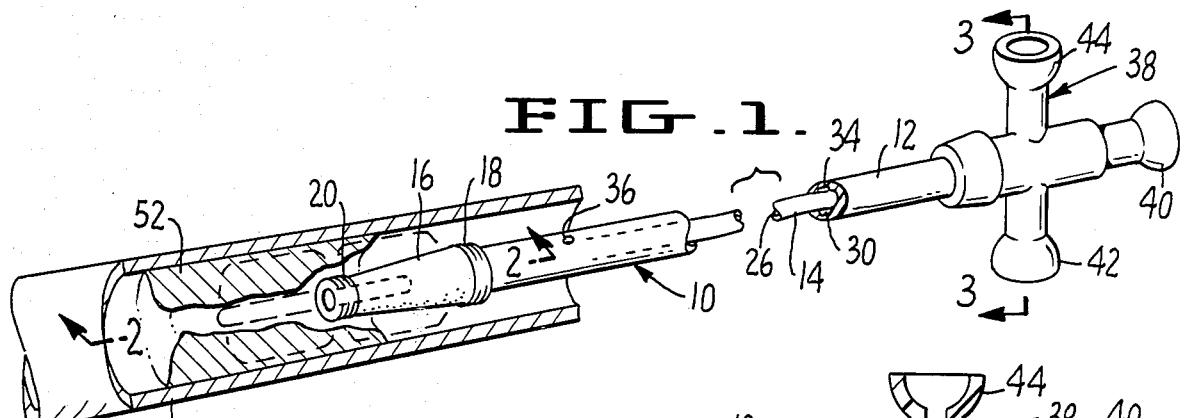
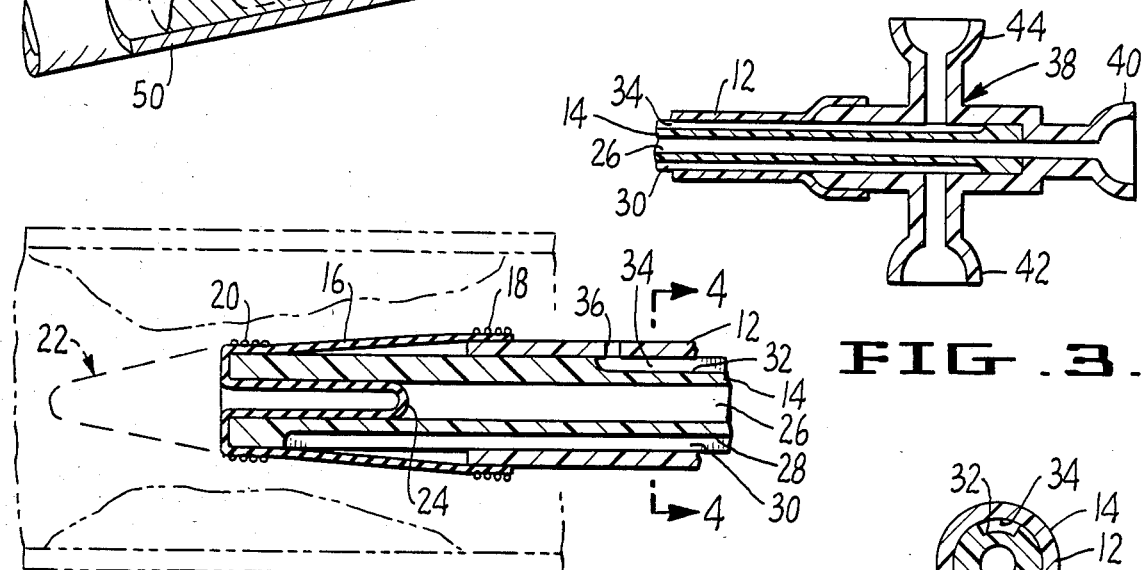
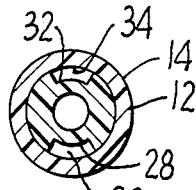
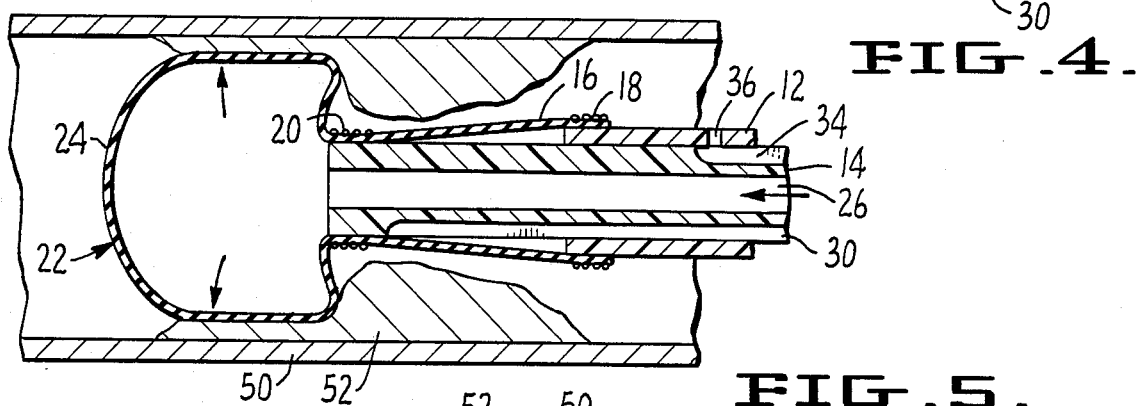
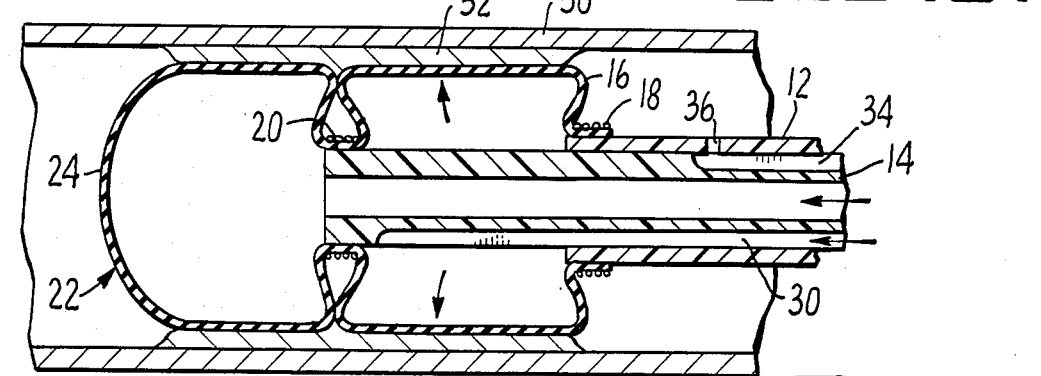

4,630,609

DILATATION CATHETER METHOD AND APPARATUS

BACKGROUND OF THE INVENTION

The subject invention relates to a method and apparatus for use in dilating occluded blood vessels. More particularly, the subject invention relates to such a method and apparatus in which dilatation is achievable through selective use of first and second balloon means. The invention is intended for use in treating either arterial or venous occlusions.

Prior art efforts for the treatment of occluded blood vessels have relied mainly upon the employment of bypass vessels or some surgical technique whereby the occlusion is physically removed from the vessel being treated. A recent technique for treating occluded blood vessels relies upon the insertion of some type of an instrument into the vessel to dilate the occlusion through a stretching or compressing process. The subject invention is concerned with a technique of the latter type.

There are balloon type dilatation catheters employing invertable-evertable balloon elements at their distal ends. Eversion of the balloon element is accompanied by its linear extrusion through the occlusion zone. Subsequent radial expansion of the balloon element serves to compress or compact the occlusion in place. Balloon elements of this type have generally a low dilating capacity and a low shape retention capacity, tending to elongate and bulge out at the sides of the occluded area when severe radial restriction is offered by hard, fibrous plaque.

Another type of balloon element in such dilatation catheters has been one of the sleeve type in which both ends of the element are anchored. Such a balloon is generally capable of applying a higher pressure to an occlusion and is better able to hold its shape than the invertable-evertable type of balloon element.

SUMMARY OF THE INVENTION

The subject invention combines in a dilatation catheter a double balloon system at the distal end of the catheter. The more distal of the two balloon elements is a balloon of the invertable-evertable type. In close proximity to this balloon element is a balloon element of the sleeve type. These balloon elements are selectively usable in a number of ways to take advantage of the properties which are special to each type of balloon element. By the eversion action of the leading balloon element the catheter works its way into an occlusion zone with a minimum tendency to plaque dislodgment and embolus formation. Following subsequent radial expansion and deflation of this leading balloon element, the following sleeve balloon element may be subjected to a higher pressure to achieve final compaction of the occlusion.

An object of the invention is to provide a dilatation catheter with a leading balloon element of the invertable-evertable type and an adjacently disposed trailing balloon element of the sleeve type.

Another object of the invention is to provide a dual balloon dilatation catheter with a triple lumen system, one lumen each for the balloon elements and the other for the injection of fluid into the blood vessel by way of a through-port.

Another object of the invention is to provide a blood vessel dilatation method characterized by low and high pressure application in sequential stages in one vessel zone or simultaneous low and high pressure application in different vessel zones.

DESCRIPTION OF THE DRAWING

FIG. 1 is a view in perspective of the subject catheter preliminarily positioned with respect to a vessel occlusion.

FIG. 2 is an enlarged view taken along lines 2—2 of FIG. 1.

FIG. 3 is an enlarged view taken along lines 3—3 of FIG. 1.

FIG. 4 is a view taken along lines 4—4 of FIG. 2.

FIG. 5 is a view showing the leading balloon element in radially inflated condition and the trailing balloon element in non-inflated condition.

FIG. 6 is a view like that of FIG. 5 but showing both balloon elements in radially inflated condition.

DESCRIPTION OF THE PREFERRED EMBODIMENT

The catheter indicated generally at 10 comprises an outer catheter 12, an inner catheter 14, a sleeve balloon 16 having its proximal end connected, as by suture attachment 18, to the outer catheter 12 and having its distal end connected, as by a suture attachment 20 to the inner catheter 14, and a balloon element 22 attached to the distal end of inner catheter 14, as by suture attachment 20 also, and having a closed end 24 adapted to be invertably enclosed within the lumen 26 of the inner catheter 14. Defined between the catheter elements 12 and 14 by a longitudinal channel 28 formed in the inner catheter element 14 is the pressure medium supply lumen 30 for sleeve balloon element 16. Defined between catheter elements 12 and 14, as by a longitudinal groove 32 formed in catheter element 14, is a third lumen 34. Through-port 36 in outer catheter element 12 is in communication with lumen 34.

A fluid supply manifold 38 is attached to the catheter. The manifold is provided with fluid supply feeding elements 40, 42 and 44 which are in communication, respectively, with lumen 26, lumen 30 and lumen 34.

In the drawing, blood vessel 50 is shown with occlusion 52.

The application of fluid pressure through element 40 to lumen 26 first causes the lengthwise expansion of balloon 22. This longitudinal expansion of the balloon enables movement of the catheter along the occlusion to position balloon 22 as desired relative to the occlusion. If the occlusion is relatively short in length and not hard and fibrous in nature, the balloon 22 alone may be employed to dilate the vessel along the full occlusion zone and thereby radially compress the occlusion. This is accomplished by boosting the pressure in balloon 22 so that it radially expands. Radial expansion of balloon 22 is illustrated in FIG. 5. Radial expansion also of balloon 16 is shown in FIG. 6. Expansion of balloon 16 is accomplished by the introduction of pressurized fluid along element 42 and lumen 30. FIGS. 5 and 6 are illustrative only of a sequential radial inflation of the two balloons and are not intended to depict a preferred mode of conjoint use of the two balloons.

One method of preferred conjoint use of the balloons is as follows. This method would be particularly appropriate where the occlusion is severe and formed of hard, fibrous plaque which is particularly resistant to being radially compressed. The occlusion is first dilated by way of radial expansion of balloon 22 alone. This balloon is then deflated. The catheter is then advanced to position balloon 16 within the occlusion zone just treated preliminarily by balloon 22. Balloon 16 is then radially expanded to accomplish the final degree of dilation desired for the occlusion zone. It will be appreciated that higher compressive forces are satisfactorily obtainable from sleeve balloon 16 than from the invert-evert balloon 22 due mainly to the fact that the free end 24 of the latter is not positionally controllable under high radial expansion pressures.

Another preferred mode of conjoint use of the two balloons is as follows. The proximal or sleeve balloon 16 is positioned adjacent the occlusion zone and is radially expanded to anchor the catheter relative to vessel 50. While maintaining the proximal balloon inflated, the distal balloon is inflated to, first, extrude it through the occlusion zone and, second, dilate the occlusion zone.

The disadvantage in providing a lengthy sleeve balloon as the sole dilatation balloon is that the catheter carrying such a sleeve balloon must be advanced through the stenosed area, thereby increasing the risks of plaque dislodgment and embolus formation. The subject combination or dual balloon dilatation catheter allows both eversion-linear extrusion and direct radial compression to occur, as required.

Manifold element 44, lumen 34 and through-port 36 constitute means whereby injections or pressure measurement can be made at any time while the catheter is in place in a vessel.

The balloons may be made of either an elastomeric material or a non-distensible polymeric material.

What is claimed is:

1. A method for dilating an occlusion within a blood vessel comprising providing a flexible catheter having at its distal end a first balloon having the mouth thereof peripherally sealed to the end of the catheter and the body thereof inverted within the catheter, providing adjacent to said first balloon a second balloon having its ends peripherally sealed to the catheter, introducing said catheter into the vessel and positioning its distal end adjacent the occlusion, radially expanding said second balloon into pressing engagement with said vessel to thereby anchor the catheter relative thereto, and while maintaining said second balloon so expanded pressurizing said first balloon to first evert the body thereof out of the catheter and extrude the same into the occlusion, and further pressurizing said first balloon to radially expand the same to dilate the occlusion.

2. A method for dilating an occlusion within a blood vessel comprising providing a flexible catheter having at its distal end a first balloon having the mouth thereof peripherally sealed to the end of the catheter and the body thereof inverted within the catheter, providing adjacent to said first balloon a second balloon having its ends peripherally sealed to the catheter, introducing said catheter into the vessel and positioning its distal end adjacent the occlusion, pressurizing said first balloon to first evert the body thereof out of the catheter and extrude the same into the occlusion, further pressurizing said first balloon to radially expand the same to dilate the occlusion, depressurizing said first balloon, moving said second balloon in depressurized condition into the dilated occlusion, and further dilating the occlusion by pressurizing said second balloon and radially expanding the same.

3. A dilatation catheter for occluded blood vessels comprising a tubular carrier, a first balloon having proximal and distal end portions attached to said carrier at the distal end portion thereof, a second balloon having a proximal end portion attached to said carrier at the distal end thereof adjacent the distal end portion of said first balloon and having a free end inverted within said carrier, and means to selectively pressurize and depressurize said balloons, said first balloon being radially expansible and contractible in response to pressurization and depressurization, said second balloon being evertable from said carrier and longitudinally expansible without substantial lateral expansion under pressurization and thereafter laterally expansible under increased pressurization.

4. The catheter of claim 3, said balloons together, when jointly expanded against an occlusion to dilate the same, constituting a substantially continuous pressurizing membrane working against said occlusion.

5. The catheter of claim 3, said tubular carrier comprising inner and outer tubular elements, the distal end of said inner element extending beyond the distal end of said outer element, said first balloon having its end portions attached to the distal end portions of said elements, said second balloon having its proximal end portion attached to the distal end of said inner element and having its free end inverted within said inner element.

* * * * *